United States Patent
Jones et al.

(10) Patent No.: US 7,402,177 B2
(45) Date of Patent: Jul. 22, 2008

(54) POLYMERIC ACETABULAR CUP

(75) Inventors: Scott A. Jones, McMurray, PA (US); Marc M. Peterman, Memphis, TN (US)

(73) Assignee: Ortho Development Corporation, Draper, UT (US)

( * ) Notice: Subject to any disclaimer, the term of this patent is extended or adjusted under 35 U.S.C. 154(b) by 355 days.

(21) Appl. No.: 11/192,513

(22) Filed: Jul. 29, 2005

(65) Prior Publication Data

US 2005/0261777 A1 Nov. 24, 2005

Related U.S. Application Data

(63) Continuation-in-part of application No. PCT/US2004/002863, filed on Feb. 2, 2004.

(60) Provisional application No. 60/444,006, filed on Jan. 31, 2003.

(51) Int. Cl.
A61F 2/30 (2006.01)
A61F 2/36 (2006.01)

(52) U.S. Cl. .................. 623/22.39; 623/22.32

(58) Field of Classification Search ............. 623/22.39, 623/22.38, 22.32, 22.23, 22.21, 22.11
See application file for complete search history.

(56) References Cited

U.S. PATENT DOCUMENTS

| | | | |
|---|---|---|---|
| 3,806,960 A | 4/1974 | Weber | |
| 3,829,904 A * | 8/1974 | Ling et al. | 623/22.39 |
| 3,864,758 A | 2/1975 | Yakich | |
| 3,894,297 A | 7/1975 | Mittelmeier et al. | |
| 4,883,490 A * | 11/1989 | Oh | 623/22.39 |
| 5,080,678 A | 1/1992 | Spotorno et al. | |
| 5,181,926 A | 1/1993 | Koch et al. | |
| 5,405,402 A | 4/1995 | Dye et al. | |
| 5,480,448 A | 1/1996 | Mikhail | |
| 5,549,699 A | 8/1996 | MacMahon et al. | |
| 5,549,701 A | 8/1996 | Mikhail | |
| 5,571,200 A | 11/1996 | Cohen et al. | |
| 5,571,201 A | 11/1996 | Averill et al. | |
| 5,658,294 A | 8/1997 | Sederholm | |
| 5,658,338 A | 8/1997 | Tullos et al. | |
| 5,735,901 A * | 4/1998 | Maumy et al. | 128/898 |
| 5,931,870 A | 8/1999 | Cuckler et al. | |
| 5,938,702 A | 8/1999 | Lopez et al. | |
| 6,136,034 A | 10/2000 | Townley | |
| 6,290,727 B1 | 9/2001 | Otto et al. | |
| 6,299,647 B1 | 10/2001 | Townley | |
| 6,676,704 B1 * | 1/2004 | Pope et al. | 623/18.11 |

* cited by examiner

*Primary Examiner*—Pedro Philogene
(74) *Attorney, Agent, or Firm*—Matthew D. Thayne; Stoel Rives LLP

(57) ABSTRACT

An orthopedic prosthesis comprising a polymeric cup member for use in a ball and socket joint is disclosed. The cup member may include several advantageous features such as a multi-directional and multi-planar channel having an undercut area that provides a mechanical lock between the cup member and a fixation material for enhanced fixation. The cup member may further comprise a plurality of spacers for ensuring an even mantle of fixation material between the cup member and the bone, a series of divots for enhancing fixation, a locating feature that permits a physician to visualize and locate the cup member in the socket of the patient's bone on appropriate medical equipment, and a lead-in chamfer located between a terminal edge and an interior surface of the cup member. Further, the terminal edge of the cup member may comprise a planar rim or may alternatively comprise a hood located distally from said terminal edge.

1 Claim, 9 Drawing Sheets

POLYMERIC ACETABULAR CUP

CROSS-REFERENCE TO RELATED APPLICATIONS

This application is a continuation-in-part of PCT Application No. PCT/US2004/002863, entitled "POLYMERIC ACETABULAR CUP," filed in the United States Patent Office and having an international filing date of Feb. 2, 2004, which claimed the benefit of U.S. Provisional Application No. 60/444,006, filed Jan. 31, 2003 entitled "POLYMERIC ACETABULAR CUP," both of which are hereby incorporated by reference herein in their entireties, including but not limited to those portions that specifically appear hereinafter, the incorporation by reference being made with the following exception: In the event that any portion of the above-referenced applications is inconsistent with this application, this application supercedes said above-referenced portion of said applications.

STATEMENT REGARDING FEDERALLY SPONSORED RESEARCH OR DEVELOPMENT

Not Applicable.

BACKGROUND

1. The Field of the Invention.

The present disclosure relates generally to an orthopedic prosthesis, and more particularly, but not necessarily entirely, to a prosthesis for implantation into a socket of a ball and socket joint of a human body.

2. Description of Related Art

The pelvis of a human generally comprises four major bones, namely two hip bones located on the front and lateral portions of the pelvis and the sacrum and the coccyx located behind the hip bones. The hip joint is formed essentially of portions of the hip bone and portions of the femur. Specifically, the hip bone is comprised of the ilium, the ischium, and the pubis, which are distinct portions in the human pelvis that start out in a person's youth as individual pieces of bone and become fused during a person's adulthood. Fusion of the ilium, the ischium, and the pubis occurs in and around the acetabulum, which is a substantially semispherical shaped, or substantially horse shoe shaped, articular cavity. The femur, which is the longest and strongest bone in the skeleton, comprises an upper and lower extremity as well as a body. The upper extremity comprises a femoral head, a femoral neck in addition to a greater and lesser trochanter. The femoral head articulates with the hip bone at the acetabulum, forming the ball and socket portions of the hip joint.

According to Henry Gray's classic text, *Anatomy of the Human Body* (1918), the movements of the hip are very extensive and comprise flexion, extension, adduction, abduction, circumduction, and rotation movements. Additionally, the hip plays an important role in weight bearing and permits a person to ambulate. Accordingly, the hip joint is subject to several various forces due to the complex movements listed above. Over time, degeneration of the hip joint is a relatively common problem that may manifest itself in various forms. Examples of such degeneration include, osteoarthritis (a process that directly results in the wearing out of cartilage on the joint surface), arthritis (a disease of the tissue that lines the inside of the joint, and results in the inflamation, stiffness and deformation of the joint), avascular necrosis (a disease where the blood supply to the femoral head of the joint is reduced), dislocation and fracture around the joint (may cause rapid degeneration of the joint), developmental dysplasia of the hip (a congenital deformity with symptoms ranging from a minor displacement of the femoral head out of the center of the acetabulum to a complete dislocation of the femoral head out of the acetabulum), as well as other anatomical deformities of the hip joint.

It is common practice for orthopedic surgeons to correct degenerative problems, or deformities of the hip joint by replacing the diseased, damaged, or otherwise compromised natural hip components with artificial prosthetic hip components. Over the years, manufacturers of prosthetic implants have attempted to imitate the biomechanics of the hip joint. More specifically, manufacturers of prosthetic implants have attempted to provide a bearing surface that may be implanted within the acetabulum with or without the need for a separate shell component, such that the implant substantially mirrors the functions of the natural articulation surfaces in the hip joint.

For example, U.S. Pat. No. 6,290,727 (granted Sep. 18, 2001 to Otto et al.) discloses an acetabular cup having an outer surface configured for resting in a cavity of the pelvis and an inner bearing surface configured for receiving a prosthetic head therein. The outer surface comprises a plurality of concentric annular grooves and a plurality of longitudinal grooves that are arranged transversely to said annular grooves exposing a plurality of surface segments therebetween. This design is disadvantageous because the surface segments formed by the grooves contain sharp edges and corners and are shaped in such a manner so as to create stress risers between the acetabular cup and the fixation material, which may cause cracking in the cement or other fixation material loosening the acetabular cup from the bone. Further, the grooves contain sidewalls that do not taper making it difficult for the cement or other fixation material to adhere to the acetabular cup.

Another example of a prosthetic implant having a bearing surface configured for direct implantation into the acetabulum is found in U.S. Pat. No. 5,549,701 (granted Aug. 27, 1996 to Mikhail). This patent discloses an acetabular cup member having an exterior surface with a plurality of annular grooves formed therein, and a plurality of grooves formed transversely to the annular grooves. The resulting configuration of the acetabular cup contains several raised segments that are sharp and have potential to cause stress risers, causing the acetabular cup to crack the surrounding cement or fixation material, thus loosening the acetabular cup from the bone. Similar to the '727 patent granted to Otto et al., the grooves of this patent lack a tapered sidewall and further lack an undercut surface that functions to enhance fixation, making it difficult to secure the acetabular cup within the bone. Therefore, this patent has several disadvantageous features that may be addressed by the present disclosure.

It is noteworthy that none of the prior art known to applicant provides a prosthetic implant capable of being directly implanted into a socket portion of a ball and socket joint that comprises a multi-directional and multi-planar recessed channel having rounded edges to decrease the occurrence of stress risers, and tapered walls that create an undercut surface for enhancing fixation between said implant and the bone cement or other fixation material. There is a long felt, but unmet need, for an acetabular cup that may be directly implanted into a socket, that is relatively inexpensive to make, simple in operation and that enhances fixation between the implant and the cement or other fixation materials to securely seat the implant within the socket.

The prior art is thus characterized by several disadvantages that are addressed by the present disclosure. The present disclosure minimizes, and in some aspects eliminates, the above-mentioned failures, and other problems, by utilizing the methods and structural features described herein.

The features and advantages of the disclosure will be set forth in the description which follows, and in part will be apparent from the description, or may be learned by the practice of the disclosure without undue experimentation. The features and advantages of the disclosure may be realized and obtained by means of the instruments and combinations particularly pointed out in the appended claims.

BRIEF DESCRIPTION OF THE DRAWINGS

The features and advantages of the disclosure will become apparent from a consideration of the subsequent detailed description presented in connection with the accompanying drawings in which.

DETAILED DESCRIPTION

Figure 1:
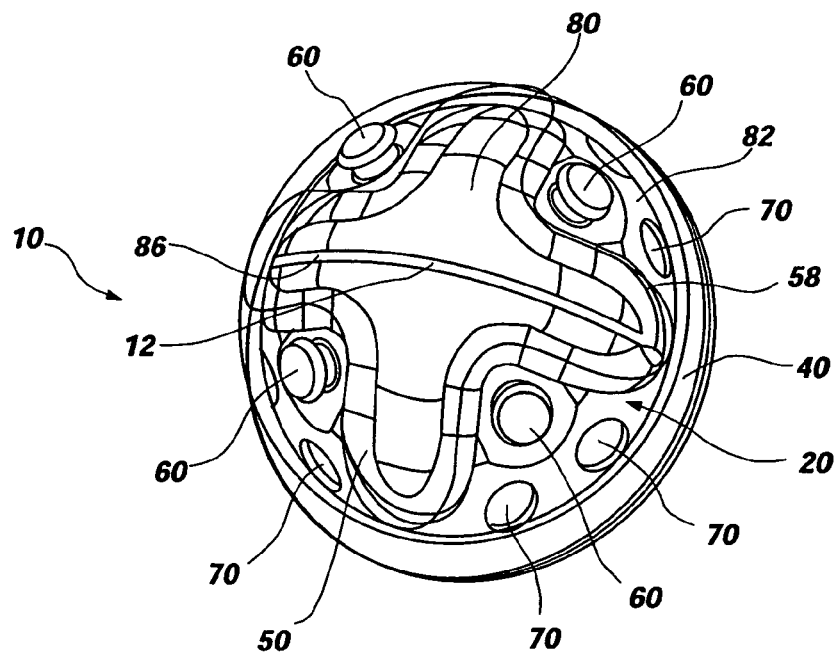
FIG. 1 is a perspective view of an acetabular cup member having four part symmetry, made in accordance with the principles of the present disclosure.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

Applicants have discovered that fixation of an acetabular cup member directly into a socket of a pelvis may be greatly enhanced by utilizing a uniquely designed acetabular cup member having, among other features, a recessed channel, formed with or without an undercut surface, that permits a fixation material, e.g., bone cement, to flow and enter into the undercut surface thereby creating a mechanical lock between the acetabular cup member and the fixation material. This unique design, which will be described hereinafter in greater detail, may enhance the fixation of the acetabular cup member within the socket of the pelvis.

Figure 2:
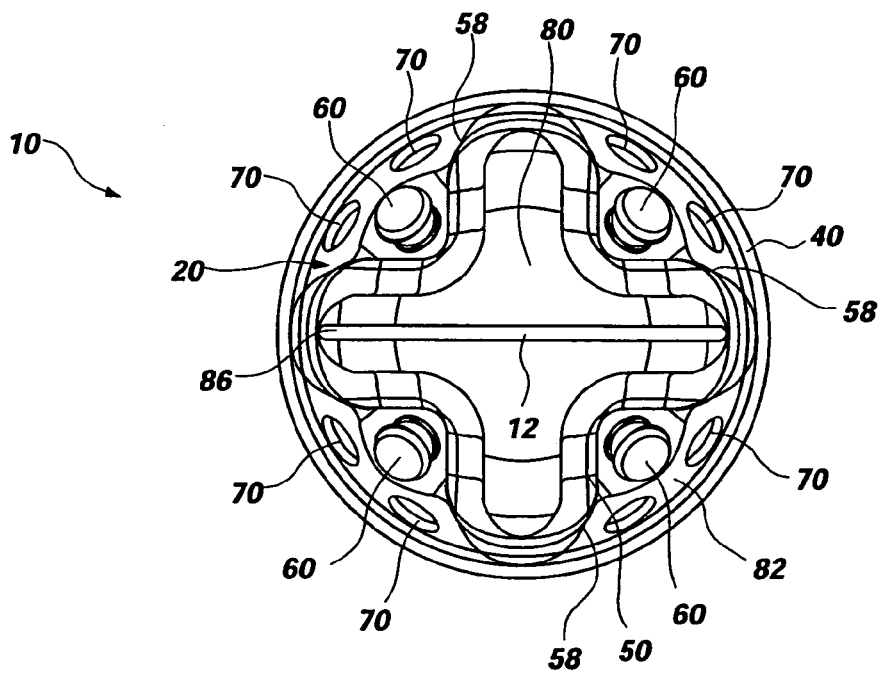
FIG. 2 is a top view of the acetabular cup member having four part symmetry, made in accordance with the principles of the present disclosure.

Referring now to FIGS. 1 and 2, wherein an acetabular cup member 10, sometimes referred to herein as cup member 10, of the present disclosure is illustrated in a perspective view and a top view, respectively. The cup member 10 of the present disclosure may be manufactured entirely from a polymeric material, such as ultra-high molecular weight polyethylene (UHMWPE), medical grade polysulfone, or poly ether ether ketone (PEEK), or other suitable polymeric material that is biocompatible and that may be configured for direct implantation in the socket of the pelvis. It will be appreciated that the cup member 10 may be manufactured such that the cup member 10 may comprise a net-shape compression molded bearing surface. It will be appreciated that net-shape compression molding may allow the bearing surface of the cup member 10 to be substantially formed directly into a final shape or state, where no further machining steps are required. It will further be appreciated that the cup member 10 may be manufactured through any compression molding process, or any injection molding process, or any cross-linking process, or any process of machining the cup member 10 from block or rod, without departing from the scope of the present disclosure.

It will also be appreciated that the present disclosure may be comprised of a cup member 10 having four part symmetry, wherein the cup member 10 may be essentially divided into four symmetric pieces. In other words, the cup member 10 may be divided into four quadrants, with each quadrant being essentially the same as the other quadrants. For example, FIGS. 1-4 illustrate a cup member 10 having four part symmetry. It will be appreciated that a four part symmetry cup member 10 may be used with a polar wire, acting as a marker 88, which will be discussed herein below in more detail. It will be appreciated that the four part symmetry may permit four point contact, and the polar wire may be used without altering the symmetry of the cup member 10.

It will be appreciated that a polar wire is a low class indication, and in certain circumstances the use of the polar wire is not justifiable on a cost basis, because of the extra cost associated with using the polar wire. In such cases, it may be more functional to use a cup member 10 having three part symmetry (discussed in more detail below). If the use of a polar wire is required or desired by the surgeon, then the cup member 10 having four part symmetry is advantageous over the cup member 10 having three part symmetry because: (i) utilizing the four part symmetry, the cup member 10 may adequately fit within the spherical recess of the bone, and the contact between the cup member 10, the fixation material, and the bone may be sufficiently strong to securely implant the cup member 10 within the acetabulum of the patient; (ii) four part symmetry also allows the polar wire to be accommodated without interrupting the other features of the cup member 10; and (iii) the four part symmetry is aesthetically pleasing.

Conversely, if the polar wire is not necessary, for cost considerations or otherwise, a cup member 10 having three part symmetry is advantageous. FIGS. 13-16 illustrate a cup member 10 having three part symmetry. Examples of the advantages of using the cup member 10 having three part symmetry include: (i) three points of contact between the cup member 10 and the bone of the acetabulum, where three point contact in an essentially spherical recess, such as the acetabulum, theoretically, works better than four point contact; and (ii) the manufacturing cost of the cup member 10 is decreased because the added expense of the polar wire is eliminated. Accordingly, in many situations a cup member 10 having three part symmetry may be advantageous over a cup member 10 with four part symmetry, and vice versa, depending upon the circumstances and whether or not a polar wire is required.

It will be appreciated that the principles of the present disclosure discussed below may be equally applied to a cup member 10 having three or four part symmetry, without departing from the scope of the present disclosure. Accordingly, the cup member 10 of the present disclosure may comprise an outer surface 20, an opposing inner surface 30 (illustrated best in FIG. 5), and a terminal edge such as a rim 40 in which said terminal edge may be partially or fully circumferential, and may comprise a rim 40 having a radially-projecting annular lip, or a lipless edge without a radially-projecting portion. The cup member 10 may further comprise a recessed channel 50, a plurality of spacers 60, and a plurality of divots 70, each of which will be explained in more detail below.

It will be appreciated that the outer surface 20 may be substantially convex, and may be referred to herein as an outer convex surface. However, it will likewise be appreciated that the outer surface 20 may be modified to include various shapes that may or may not be considered to be convex without departing from the scope of the present disclosure. The outer surface 20 may be configured and arranged for direct implantation into the socket of a patient's bone, for example the socket of the pelvis. The outer convex surface 20 may be dimensioned in a substantially partially-spherical shape. As used herein, "substantially partially-spherical" may refer to: (i) a partial sphere that is symmetrical and approximately half of a spherical object as divided by a plane of symmetry, or it may refer to: (ii) a partial sphere that is oblong, or it may refer to: (iii) a partial sphere that is elongated in any of the following directions with respect to a longitudinal axis, proximal, distal, anterior, posterior, medial and/or lateral, or it may refer to: (iv) a portion of a sphere, whether less than or more than half of the sphere, or it may refer to: (v) a portion of a sphere having a nonsymmetrical portion in at least one plane, such as a hood 90 extending from and below the rim 40 creating a nonsymmetrical, yet substantially partially-spherical outer surface 20. It will be appreciated that the shape of the cup member 10 will be largely determined by the shape of the outer convex surface 20 and may be substantially partially-spherical as well.

It should be noted that the outer convex surface 20 may comprise several features of the present disclosure that enhance the overall fixation of the cup member 10 to a fixation material within the bone. As used herein, the phrase "fixation material" may include the following types of materials: bone cements, whether acrylic or otherwise, adhesives, epoxies, bone that may grow into the implant, or proteins, or other tissues that may grow into the implant to secure the implant to the socket of the patient's bone, as well as any other suitable material currently known, or which may become known in the future, in the art for securing the cup member 10 to the socket of the bone. As illustrated in FIGS. 1 and 2, the outer convex surface 20 may comprise the recessed channel 50, the spacers 60, and the divots 70. Additionally, the outer convex surface 20 may comprise a first raised portion 80 and a second raised portion 82, where the term "raised" is defined relative to the recessed channel 50.

Figure 5:
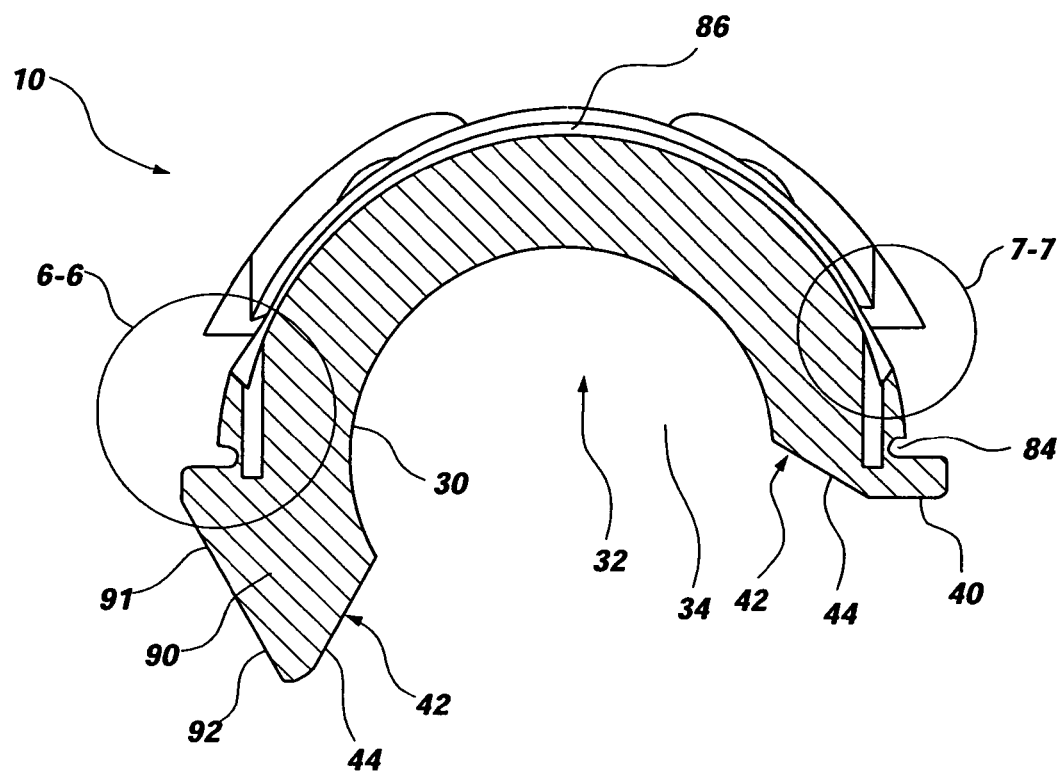
FIG. 5 is side, cross-sectional view of the acetabular cup member of FIGS. 4 and 5, made in accordance with the principles of the present disclosure.

Referring now to FIG. 5, the inner surface 30 may be substantially concave, and may be referred to herein as an inner concave surface. However, it will be appreciated that the inner surface 30 may be modified to include various shapes that may or may not be considered to be concave without departing from the scope of the present disclosure. The inner surface 30 may be configured and arranged as a bearing surface for receiving a head of a femoral prosthesis (not illustrated in the figures) therein. The inner concave surface 30 may define a cavity 32, or a hollow 32, of the acetabular cup 10 that may be substantially partially-spherical in shape such that the inner concave surface 30 may contact the head of the femoral prosthesis in an articulating engagement.

The outer convex surface 20 and the opposing inner concave surface 30 of the acetabular cup 10 may be adjoined together by, and may together form, the rim 40, which may also be referred to herein as the circumferential rim 40 or an annular rim 40, as the rim 40 may or may not completely circumscribe the opening of cup member 10. The rim 40 may define an opening 34 to the cavity 32. The rim 40 may be associated with a lead-in chamfer 42 (illustrated best in FIG. 5).

The lead-in chamfer 42 may be formed at a junction between the inner concave surface 30 and the rim 40 of said cup member 10. The lead-in chamfer 42 may comprise a tapered wall 44 that may circumscribe, or delimit, at least a portion of the opening 34. The lead-in chamfer 42 may be configured and dimensioned for increasing the range of motion of the femoral prosthesis by allowing a neck portion of the femoral prosthesis (not illustrated in the figures) to move through a greater range of motion than if the lead-in chamfer 42 were not present. Specifically, as the head portion of the femoral prosthesis articulates within the inner concave surface 30 of the cup member 10, the neck portion of the femoral prosthesis may move to an extreme position relative to the cavity 32. It will be appreciated that the neck portion of the femoral prosthesis may move in tandem with said head portion to the extreme position within the cavity 32 without prematurely interfering with the inner surface 30 of the cup member, thus inhibiting the movement of said head portion due to the shape of the lead-in chamfer 42. In other words, the lead-in chamfer 42 permits the neck portion to move farther within the cavity 32 before contacting the tapered wall 44 of the lead-in chamfer 42 than if the lead-in chamfer 42 and tapered wall were not present, thus increasing the range of motion of the femoral prosthesis within the cavity 32.

Figure 3:
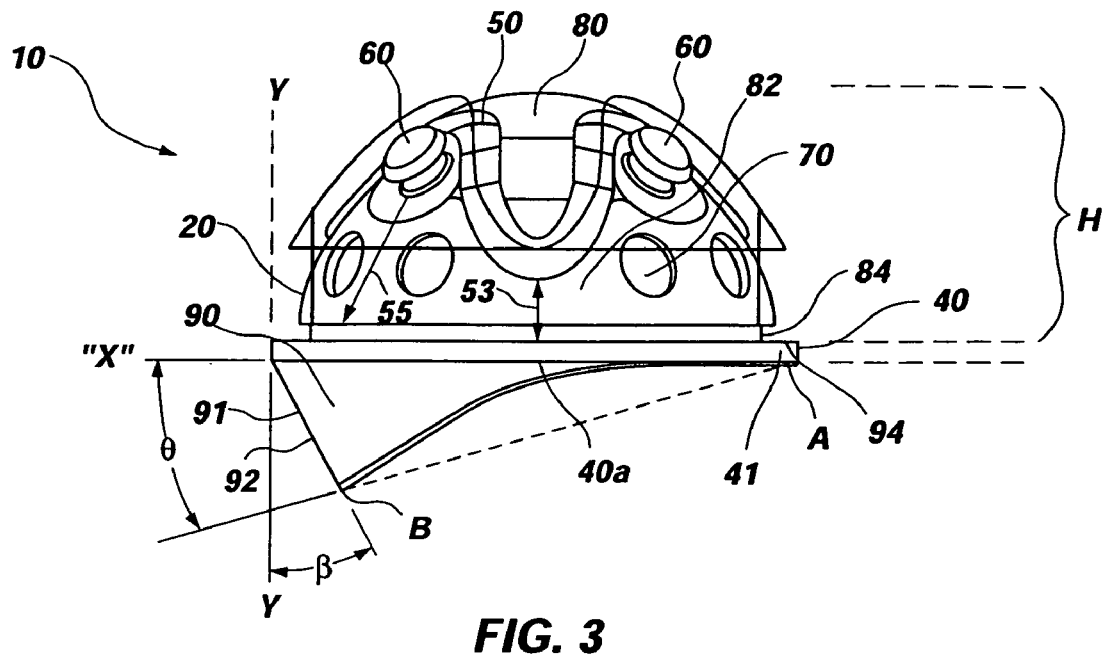
FIG. 3 is a side view of the acetabular cup member of FIGS. 1 and 2, particularly illustrating a hood, made in accordance with the principles of the present disclosure.
Figure 4:
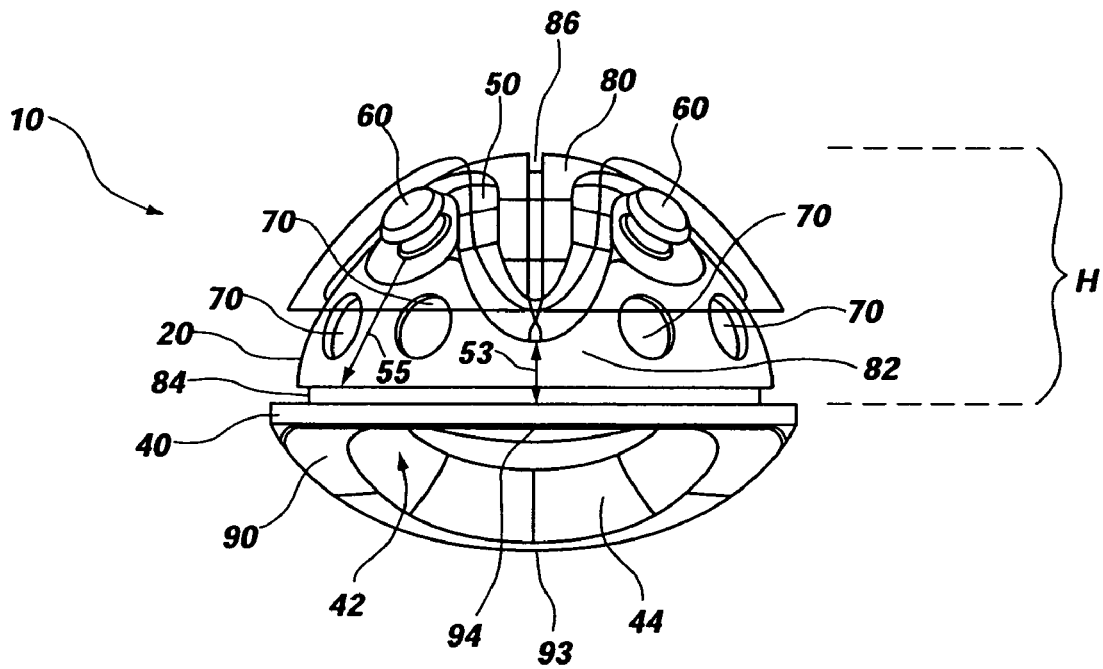
FIG. 4 is a side view of the acetabular cup member of FIG. 3 rotated ninety degrees from the position of FIG. 3.

Referring now to FIGS. 3-5, wherein the cup member 10 is illustrated in three different side views. Illustrated particularly therein is the hood 90 that may extend below the rim 40. It will be appreciated that the hood 90 may be formed as an integral part of the rim 40, and may extend at an angle θ, with respect to a horizontal axis "X," from approximately a mid-section 40*a* of said rim 40 (illustrated best in FIG. 3). It will be appreciated that the hood 90 may begin to extend before or after the mid section 40*a* of the rim 40 without departing from the scope of the present disclosure. For example, as illustrated in FIG. 3, the hood 90 may begin to extend below the rim 40 at a section of the rim 40 that may be located anteriorly, which in this view is on the right side of the page, with respect to the mid section 40*a*. It will be appreciated that the angle θ may be measured from a reference point A located opposite the hood 90 on an outer portion 41 of said rim 40 to a point B located opposite point A on a bottom edge of the hood 90 as illustrated in FIG. 3. It should be noted that the angle θ may be within a range of about one degree to about forty-five degrees. For example, an angle of about fifteen degrees to about twenty-five degrees has been found to be an appropriate angle for the hood 90, but it should be noted that any angle within the given range may be utilized by the present disclosure, and is intended to fall within the scope of the present disclosure.

As illustrated in FIGS. 3 and 5, the hood 90 may comprise an outer surface 91 having a taper 92, wherein the taper 92 may comprise an angle β that may be within a range of about zero to about forty-five degrees, with respect to a line Y-Y that is parallel to a longitudinal axis of the cup member 10. For example, an angle of about thirty degrees has been found to be appropriate for the angle β. However, it should be noted that any angle falling within the given range is contemplated by the present disclosure and intended to fall within the scope of the present disclosure.

It will be appreciated that the hood 90 may be advantageously placed in the superior-posterior or inferior-anterior regions of the pelvis, and care should be taken to locate the hood 90 as near as possible in the posterior portion of the pelvis. The cup member 10 may comprise a hood marker 94 that may be located opposite the hood 90, and may be approximately 180° from a central portion 93 of the hood 90 (illustrated best in FIG. 4) to aid the surgeon in locating the hood 90 in the posterior most position in the pelvis. The hood marker 94 may function to provide a characteristic label that may be visualized by appropriate medical equipment so that the surgeon may identify where the hood 90 has been located in the pelvis. It will be appreciated that the hood marker 94 may be a protrusion comprising a tag or label, or it may be a recess having a tag or label placed therein, or it may be any other location feature that is currently known, or which may become known in the future, in the art to provide a characteristic mark such that the hood marker 94 may be visible on X-rays, ultrasounds, and other procedures used for visualizing internal organs and tissues of the body, utilizing appropriate medical equipment to perform such procedures.

Figure 6:
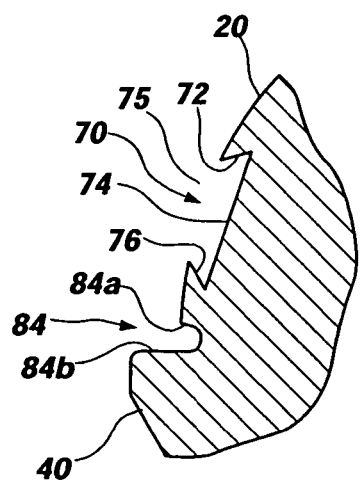
FIG. 6 is an enlarged break-away view of a reference plane spaced apart from the area labeled 6-6 of FIG. 5 and passing through a divot, illustrating a groove and the divot of the acetabular cup member, made in accordance with the principles of the present disclosure.

Referring now to FIG. 6, wherein an enlarged break-away view of the box labeled 6-6 in FIG. 5 illustrates the particulars of a first groove 84 and the divot 70. It will be appreciated that the first groove 84 may or may not completely circumscribe the cup member 10, and may comprise an upper surface 84*a* and a lower surface 84*b*, wherein the upper surface 84*a* and the lower surface 84*b* may define the shape of the groove 84.

It will be appreciated that the lower surface 84*b* of the first groove 84 may also form a part of the rim 40. Specifically, the lower surface 84*b* of the groove 84 may form part of an upper surface of the rim 40. In other words, the first groove 84 and the rim 40 may share a common surface 84*b*. The first groove 84 may be configured and arranged for accommodating and receiving a marker 88 (illustrated best in FIG. 11) therein, such that a physician may utilize the marker 88 to position, locate, and visualize the cup member 10 on an X-ray film, ultrasound, or any other suitable means for visualizing the cup member 10 after it has been implanted in the socket of the patient's bone. It will be appreciated that the shape of the first groove 84 may be substantially round or circular as illustrated, or it may be substantially polygonally shaped, or it may be any other suitable shape for accommodating and receiving the marker 88 therein.

In addition to the first groove 84, the cup member 10 may also comprise a second groove 86, which may be a longitudinal groove, illustrated in FIGS. 1, 2 and 4. The second groove 86 may be disposed within the first raised portion 80 of the cup member 10. It will be appreciated that the second groove 86, may extend from one side of the first raised portion 80 through a pole 12 of the cup member 10 to another side of the first raised portion 80 as illustrated in FIGS. 1 and 2. The pole 12 may be defined as an extremity of a central axis running through the center of the partially-spherical cup member 10, as illustrated in FIGS. 1 and 2. However, it should be noted that the second groove 86 may be modified such that it does not extend through the pole 12 of the cup member 10, but may circumvent the pole 12 completely, or may pass through only a portion of said pole 12, without departing from the scope of the present disclosure.

Figure 7:
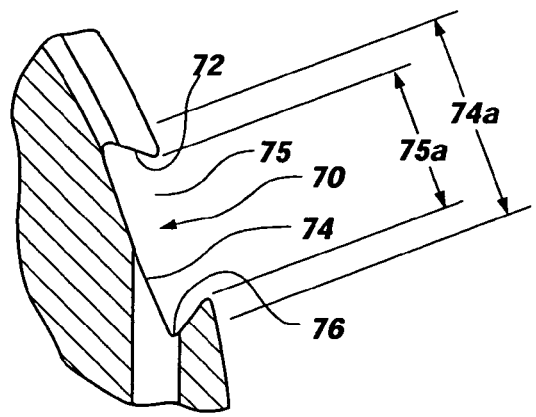
FIG. 7 is an enlarged break-away view of a reference plane spaced apart from the area labeled 7-7 of FIG. 5 and passing through the divot, illustrating an undercut surface of the divot of the acetabular cup member, made in accordance with the principles of the present disclosure.

Referring now to FIGS. 6 and 7, the cup member 10 may comprises a plurality of divots 70 referred to above. The plurality of divots 70 may be evenly spaced on the outer convex surface 20, and may be located distally with respect to the recessed channel 50. It will be appreciated that the divots 70 may be located in a symmetrical or non-symmetrical manner on the outer convex surface 20 of the cup member 10, and may or may not be evenly spaced apart. For example, a cluster of two or more divots 70 may be located distally with respect to the channel 50 in a scattered arrangement, or the divots 70 may be evenly spaced apart in a very defined pattern, as illustrated in FIG. 2, without departing from the scope of the present disclosure.

It will be appreciated that each divot 70 may be defined by a tapered wall 72 and a recessed surface 74. The tapered wall 72 may include a free end that defines an opening 75 to said divot 70, with said wall 72 tapering toward the recessed surface 74, such that the opening 75 may be smaller than the recessed surface 74, as illustrated in FIG. 6. It will be appreciated that the recessed surface 74 may be placed shallower or deeper in the outer convex surface 20 by modifying the height of the tapered wall 72. As illustrated, the divots 70 may be substantially rounded depressions that aid in securing the cup member 10 to the socket of the bone. It will be appreciated, however, that the divots 70 may be modified to include other shapes, including oval, triangular, square, polygonal, or any other suitable shape, as long as the function of the divots 70 is maintained.

It is to be understood that the divot 70, as illustrated, may be round and therefore comprises a single tapered wall 72, but the single tapered wall 72 will necessarily change and may become multiple tapered walls 72 as the shape of the divot 70 is changed. The tapered wall 72 may taper outwardly as illustrated in FIGS. 6 and 7, such that an undercut surface area 76 defined by surface 72 may be formed beneath the opening 75 of the divot 70. The undercut surface area 76 of the divot 70 may be configured and arranged for receiving the fixation material therein, and for forming a mechanical lock between said fixation material and the tapered wall 72 of the divot 70, to thereby enhance the fixation of the cup member 10 within the socket of the bone. It will be appreciated that such an undercut surface area 76 may or may not be present in the design of the cup member 10, without departing from the scope of the present disclosure. It will be appreciated that the opening 75 may comprise a width 75a that may be smaller than a width 74a of the recessed surface 74 as illustrated in FIG. 7.

Figure 8:
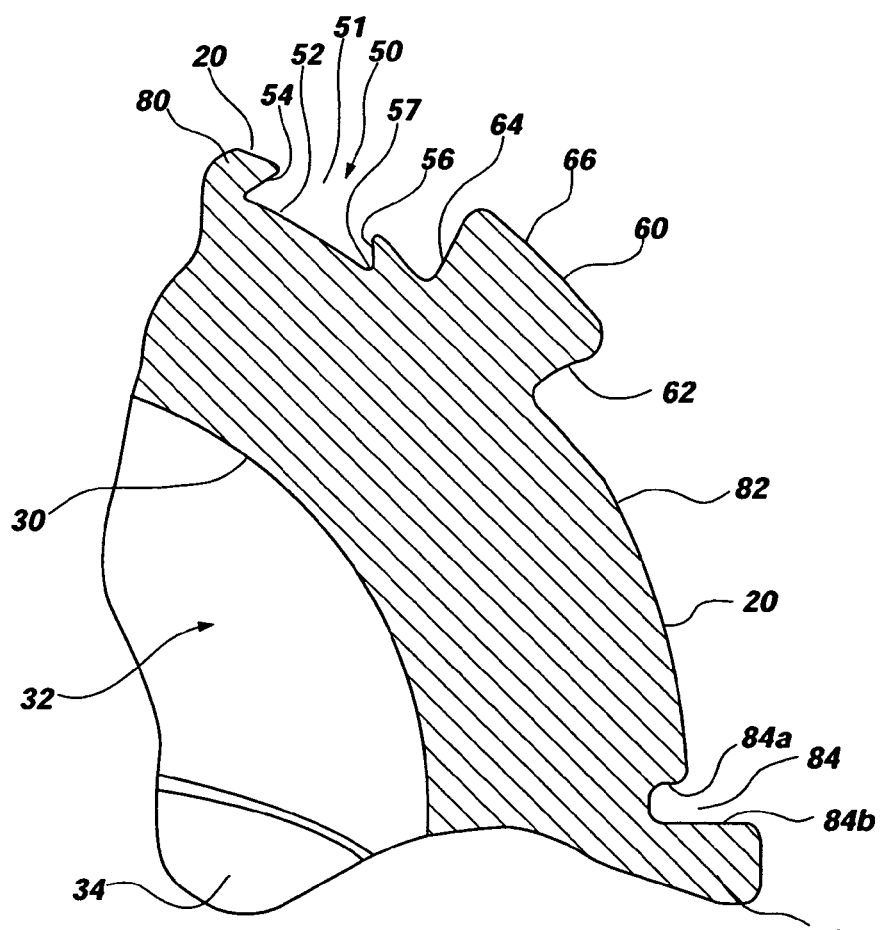
FIG. 8 is an enlarged break-away view of a portion of FIG. 5, illustrating a spacer of the acetabular cup member, made in accordance with the principles of the present disclosure.

Referring now to FIG. 8, wherein an enlarged break-away view of the cup member 10 is illustrated. More particularly, the recessed channel 50, the spacer 60, and the first groove 84 are each illustrated as being located on the outer convex surface 20 of the cup member 10. It will be appreciated that the recessed channel 50 may comprise a recessed surface 52, sometimes referred to herein as a bottom 52 of the channel 50, a first wall 54, and a second wall 56, which together may define and form the recessed channel 50. The channel 50 may be formed in the outer convex surface 20 of the cup member 10, such that a distance between the rim 40 and the channel 50 may vary between a minimum 26 and a maximum 24 as the channel 50 may extend in a partially latitudinal direction around the outer convex surface 20, as explained below in more detail. It is to be understood that the distance between the rim 40 and the channel 50 may also be described to vary between at least one minimum 26, which may also be referred to herein as a minimum distance, and at least one maximum 24, which may also be referred to herein as a maximum distance, as the channel 50 may extend in a partially latitudinal direction around the outer convex surface 20.

As used herein, the term "latitudinal direction" means forming a plane that is perpendicular to a central polar axis of the cup member 10, such that a portion of a channel that extends in the latitudinal direction thereby resides common with or parallel to such a plane. It will, therefore, be appreciated that "partially latitudinal direction" may refer to a situation in which the channel 50 is not limited only to extending around the outer surface 20 of the cup member 10 in a latitudinal direction, but may also have a longitudinal component of direction. In other words, the channel 50 may extend around the outer surface 20 of the cup member 10 such that said channel 50 varies in directional both latitudinally and longitudinally with respect to the rim 40, thereby extending in a partially latitudinal direction, as well as in a partially longitudinal direction. Further, the at least one channel 50 may be described as extending over the outer surface 20 in a curvilinear manner, as defined below, as well as in a partially latitudinal direction, or in a partially longitudinal direction. If the at least one channel 50 extends about the outer surface 20 in an at least partially latitudinal direction, it is thereby also extending in an at least partially longitudinal direction.

It will be appreciated that the recessed channel 50 may separate the first raised portion 80 from the second raised portion 82, such that said first raised portion 80 may be located inside of, and may be delimited by, the first wall 54 of said recessed channel 50. It will likewise be appreciated that the second raised portion 82 may be located outside of, and at least partially delimited by, the second wall 56 of said recessed channel 50. As noted above, the term "raised," as used herein as part of the first raised portion 80 and the second raised portion 82, may be defined as a surface that is raised above another surface. Specifically, the first and second raised portions 80 and 82 have surfaces that are raised above the recessed surface 52 of said channel 50.

It will be appreciated that the first wall 54 and the second wall 56 may each be tapered walls, such that an undercut surface may be formed beneath the convex outer surface 20. Those of skill in the art will appreciate that such an undercut surface may or may not be present, without departing from the scope of the present disclosure. The recessed channel 50 may be a curvilinear channel that extends over the outer convex surface 20 of the cup member 10 in a plurality of directions, i.e. multi-directional, and through a plurality of planes, i.e. multi-planar. It will be appreciated that the recessed surface 52 and the first wall 54 and the second wall 56 of the curvilinear channel 50 may form one continuous track that may extend around the outer convex surface 20 in multiple planes.

The cup member 10 may comprise a concavo-convex cup body 14 that may be comprised of the convex outer surface 20 and the concave inner surface 30. The concavo-convex cup body 14 may have the curvilinear channel 50 formed therein for receiving fixation material thereinto. The channel 50 may extend in a partially latitudinal direction over the concavo-convex cup body 14, as illustrated, inter alia, in FIGS. 1-2 and 13-14.

As used herein the term "curvilinear" may refer to a channel 50 that is formed, bounded, or characterized by curved wall portions or segments. Additionally, as used herein the phrase "substantial loop" may include a channel 50 that is continuous, or interrupted, and may refer to the channel 50 as being enclosed on all sides except one, and may be formed in the outer convex surface 20 in an arcuate, curved, or looping manner, such that the channel 50 forms a smooth fixation groove that is characterized by the absence of sharp edges.

It will be appreciated that the multi-directional and multi-planar aspects of the channel 50 may permit three dimensional locking of the cup member 10 to the fixation material to occur. The three dimensional locking may occur as the fixation material may be located within the channel 50, which extends in a three dimensional manner across the outer surface 20 of the cup member 10, causing a connection between the channel 50 of the cup member 10 and the fixation material in three dimensions.

It will be further appreciated that the first wall 54 and the second wall 56 of the curvilinear channel 50 may extend around the outer convex surface 20 of the cup member 10, such that the curvilinear channel 50 may substantially form a cross shape in the outer convex surface 20 when visualized or examined from a perspective and top view, as illustrated in FIGS. 1 and 2. However, it should be noted that the curvilinear channel 50 may be modified to include other curvilinear shapes and is not limited to a cross. For example, any shape that is curvilinear and multi-planar may be used as the shape for the channel 50, such as a bell shape or a triangular shape or any other polygonal shape.

Additionally, the channel 50, whether used in an embodiment that may comprise concentric channels 50 (discussed below) or otherwise, may comprise various cross-sectional shapes without departing from the scope of the present disclosure. For example, the channel 50 may have multiple cross-sectional shapes such as partially circular, partially triangular, or partially polygonal or any other shape that is known, or that may become known, in the art for forming a channel. Therefore, the cross-sectional shape of the channel 50 may be modified into various shapes without departing from the scope of the present disclosure.

It will be appreciated by those skilled in the art that the existence of stress risers is a concern for surgeons and manufacturers of orthopedic devices. Stress risers may develop where sharp corners or edges of the implant contact the bone, cement, or any other fixation material placing an extra load at that sharp corner or edge, which may cause the stress riser to occur. Stress risers are problematic because loads are not efficiently transferred, such that when a stress riser does occur at said sharp corner or edge, the inefficient transfer of the load places too much stress on a single point causing the bone, cement or other fixation material, or the implant itself, to fracture or crack. Ultimately, the fracture or crack may cause the implant to fracture or loosen from said bone, cement, or other fixation material, causing the implant to fail. The present disclosure may inhibit the occurrence of stress risers in the recessed channel 50 due to the lack of sharp edges or corners, and because of its shape. The curvilinear channel 50 may wind around substantially the outer convex surface 20, without creating sharp corners or edges. The recessed channel 50 may comprise rounded, smooth edges 58, and may be further characterized by the absence of sharp edges so as to inhibit the occurrence of stress risers. It will therefore be appreciated that the overall shape of the recessed channel 50 may be as illustrated in FIGS. 1 and 2, or it may be any other curved shape that avoids the use of sharp edges and corners and replaces them with curves and rounded corners that contact the bone, cement, or other fixation material in a more uniform manner thereby efficiently transferring loads, and inhibiting the occurrence of stress risers.

Figure 10:
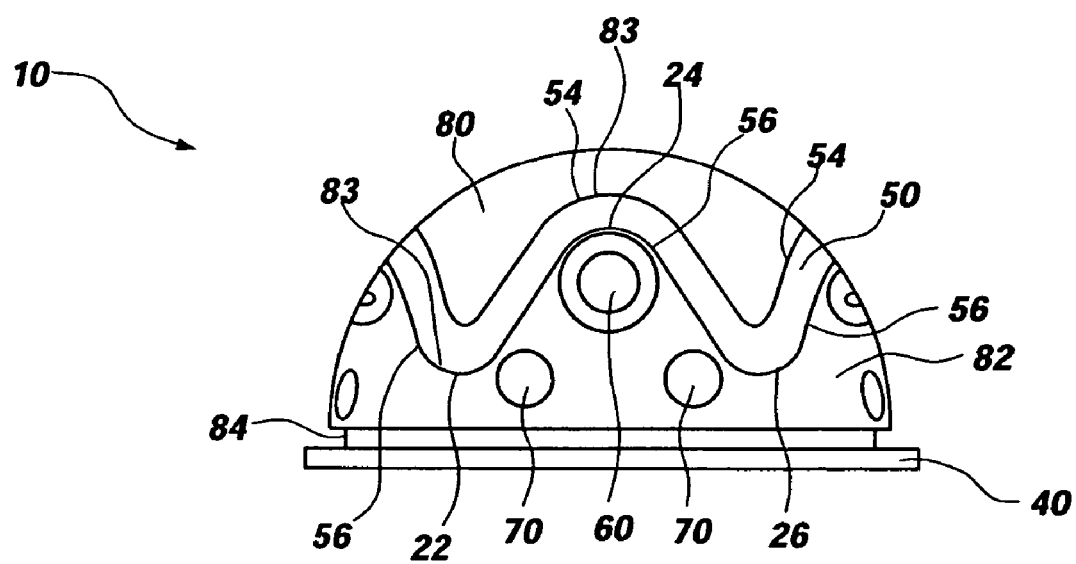
FIG. 10 is a side view of the alternative embodiment of the acetabular cup member of FIG. 9, made in accordance with the principles of the present disclosure, wherein a recessed channel, having relative minima and maxima, is particularly illustrated.
Figure 13:
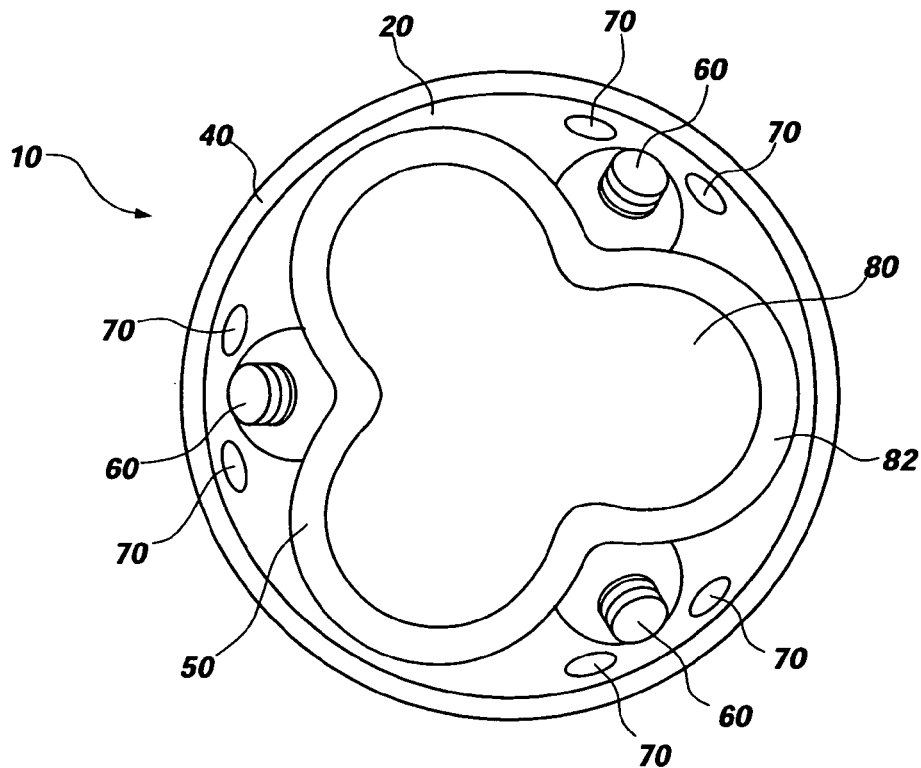
FIG. 13 is a top view of an acetabular cup member having three part symmetry, made in accordance with the principles of the present disclosure.
Figure 14:
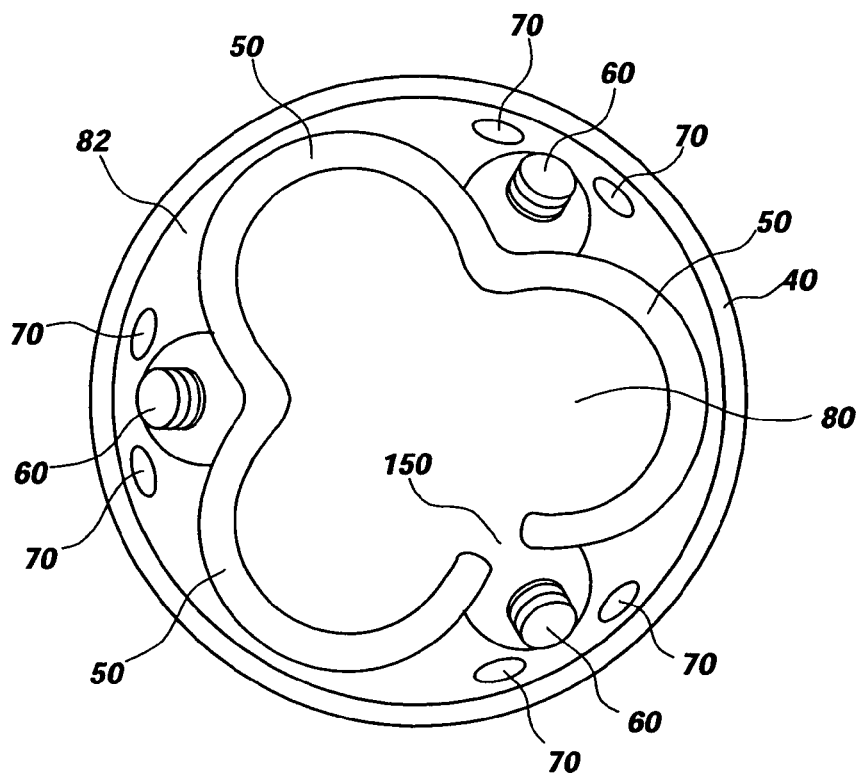
FIG. 14 is a top view of the acetabular cup member having three part symmetry and an interrupted channel, made in accordance with the principles of the present disclosure.
Figure 15:
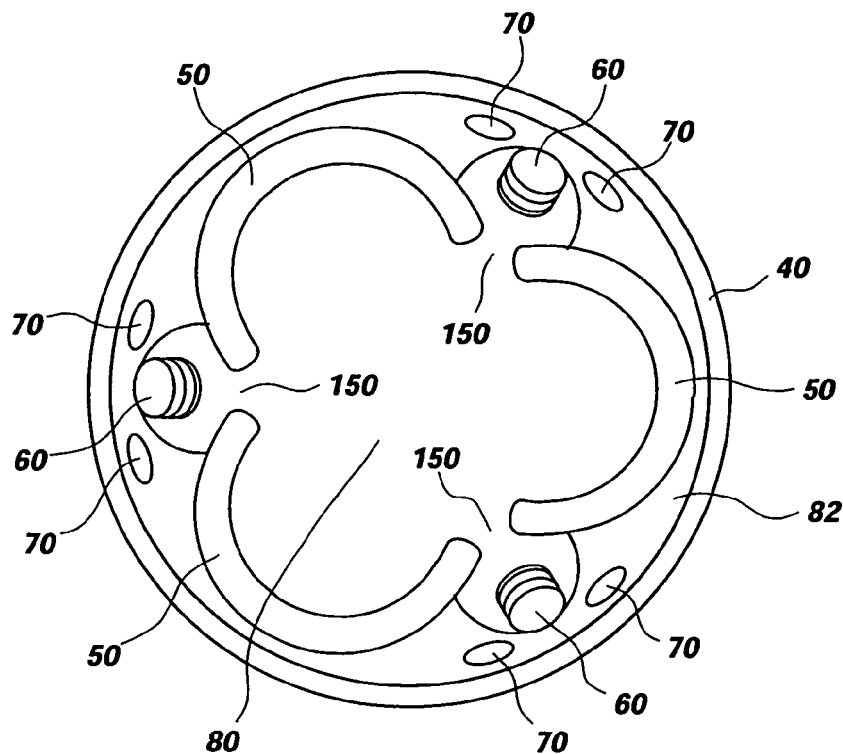
FIG. 15 is a top view of the acetabular cup member having three part symmetry and several interrupted channels, made in accordance with the principles of the present disclosure.
Figure 16:
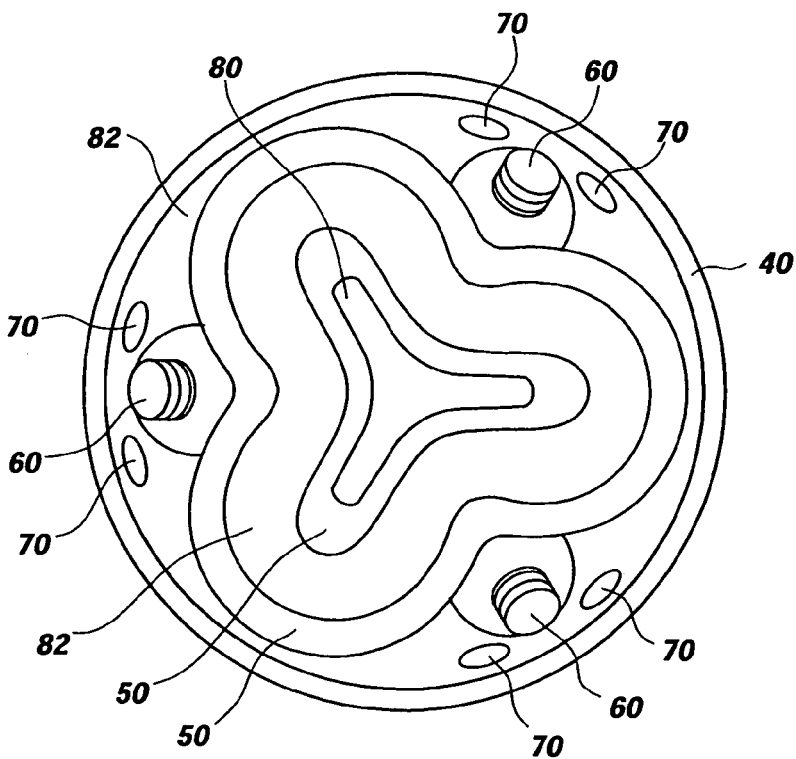
FIG. 16 is a top view of the acetabular cup member having three part symmetry and multiple concentric channels, made in accordance with the principles of the present disclosure.

Referring now to FIGS. 8 and 10, the recessed channel 50 may extend over the outer surface 20 in a single, continuous channel. It should be noted that the channel 50 may also be an endless curve, as illustrated best in FIGS. 1-2, and 13. It will be appreciated that the recessed channel 50 may be a single, continuous channel that may be utilized in either a three or four part symmetry cup member 10, as illustrated in FIGS. 1-2, and 13, or it may be a single channel interrupted by a gap 150 (illustrated best in FIG. 14), or it may be a series of interrupted curves (illustrated best in FIG. 15) forming the channel 50, wherein the interruptions may be in the form of gaps 150. It will be appreciated that other configurations of the channel 50 may be utilized by the present disclosure without departing from the scope of the present disclosure, and the above serves merely as examples of some of the possibilities that could be used to form the channel 50. However, it should be noted that the above examples are not exhaustive of the many possibilities that may be used as the channel 50.

The first wall 54 may separate the first raised portion 80 from the recessed surface 52 and the second wall 56 may separate the second raised portion 82 from the recessed surface 52, thereby substantially defining the shape of the recessed channel 50. The channel 50 and the first and second walls 54, 56 may essentially extend around the outer convex surface 20 in a non-linear fashion, or, as described above, in a curvilinear fashion. It will be appreciated that the recessed channel 50 may be one continuous channel, as illustrated in FIGS. 1 and 2, or the recessed channel 50 may be a plurality of concentric continuous channels 50 formed in the outer convex surface 20 of the cup member 10, as illustrated best in FIG. 16. It will be appreciated that each of the channels 50 of the present disclosure, whether concentric channels 50 or otherwise, may be: (i) a continuous channel, or (ii) an interrupted channel, or (iii) a discontinuous channel, or (iv) any combination of an interrupted, or discontinuous, channel may be used together with a continuous channel or channels to form the concentric channel 50 arrangement. Further, it will be appreciated each of the channels 50, whether concentric channels 50 or otherwise, may comprise different shapes, where each shape may be one of a plurality of shapes that is known, or that may become known, in the art without departing from the scope of the present disclosure. For example, each of the channels 50, whether concentric channels 50 or otherwise, may extend over the outer surface 20 of the cup member 10 such that the channel 50 or channels 50 may substantially form a cross shape in the outer surface 20, when visualized or examined from a perspective and top view. However, it should be noted that each of the channels 50, whether concentric channels 50 or otherwise, may be modified to include other shapes and is not limited to a cross. For example, any shape that is curvilinear and that may extend in a partially latitudinal direction over the outer surface 20 may be used as the shape for each of the channels 50, such as a bell shape or a triangular shape or any other polygonal shape.

As mentioned above, there may exist a distance between the rim 40 and the channel 50 that may vary between the minimum 26 and the maximum 24. Particularly referring to FIG. 10, and starting from a reference point 22, which may also be a relative minimum, of the recessed channel 50 on the outer convex surface 20 of the cup member 10, the channel 50 may increase from the reference point 22 to the relative maximum 24. The relative maximum 24 may be defined as the greatest distance from the rim 40 to the farthest point on the second wall 56 of the channel 50 in a given area of the cup member 10. Thus the relative maximum 24 has the greatest value of all the values in said given area. In other words, the relative maximum 24 may be a point on the second wall 56 of the channel 50 having a value, determined by the distance between the rim 40 and the given point on the second wall 56 of the channel 50, that is greater than the values of any of the points immediately surrounding it on the second wall 56 of the channel. The relative maximum 24 may also be defined as the farthest point away from the rim 40, said point being located on a curve of the second wall 56 of the channel 50, such that the slope of the tangent line is zero.

The channel 50 may vary between the relative maximum 24 and the relative minimum 26, such that there may be intermediate curves that do not form either a maximum 24 or a minimum 26, or the channel 50 may decrease from the relative maximum 24 to the relative minimum 26, without departing from the scope of the present disclosure. No matter what the course of the channel 50 may be across the outer surface 20, it will be appreciated that at some point the channel 50 may decrease to the relative minimum 26. The relative minimum 26 may be defined as the distance between the rim 40 and the point on the second wall 26 of the channel 50 that has the smallest value in a given area. In other words, the minimum may be defined by the point on the second wall 56 of the channel 50 that is closest to the rim 40 in a given area of the cup member 10, and thus has the lowest value of all the values in said given area. The relative minimum 26 may be a point on the second wall 56 of the channel 50 having a value that is less than the values of any of the points immediately surrounding it on the second wall 56. The relative minimum 26 may also be defined as the closest point to the rim 40, said point being located on a curve of the second wall 56 of the channel 50, such that the slope of the tangent line is zero. Therefore, it will be understood that the relative maximum 24 will have a greater value than the relative minimum 26.

It will be appreciated that there may be at least one relative maximum 24 and at least one relative minimum 26 as defined above on the channel 50. It will likewise be appreciated that there may be more than one relative maximum 24 and more than one relative minimum 26. It will further be appreciated that the values of the distances of each of the relative maxima 24 and each of the relative minima 26 may be the same value, or the values may be different without departing from the scope of the present disclosure. Additionally, it will be appreciated that the channel 50 may extend around the outer surface 20, such that the maximum 24 does not necessarily have to be directly followed by a minimum 26. In other words, the maximum 24 or the minimum 26 may be followed by an intervening value that is neither a maximum 24 nor a minimum 26 in a given area, but nevertheless proceeds to either a maximum 24 or a minimum 26 in that given area.

Figure 10A:
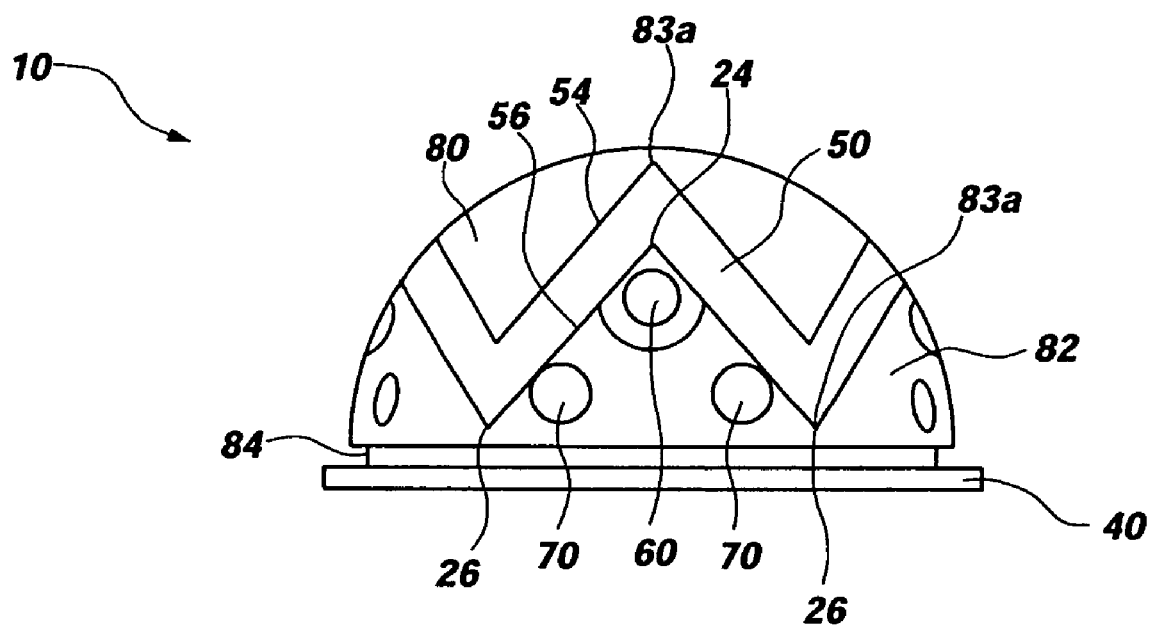
FIG. 10A is a side view of an alternative embodiment of the acetabular cup member illustrating a recessed channel that peaks to a maximum and also comprises a minimum, made in accordance with the principles of the present disclosure.

Referring now to FIGS. 10 and 10A, it will be appreciated that the cup member 10 may comprise a channel 50, or concentric channels 50, that may: (i) have an even, smooth transition area 83 near the maximum 24 and the minimum 26, or (ii) peak at the maximum 24 forming an abrupt change in the channel 50 as illustrated in FIG. 10A. In other words, FIG. 10A may have a transition area 83a relative to the first wall 54 or the second wall 56 of the channel 50 that may be more abrupt than the corresponding transition 83 in FIG. 10.

It will be appreciated that the cup member 10 may comprise three part symmetry, such that the cup member 10 may have three minima 26 and three maxima 24. Conversely, the cup member 10 may comprise four part symmetry, such that the cup member 10 may have four minima 26 and four maxima 26.

As illustrated in FIGS. 3 and 4, the cup member 10 of the present disclosure may comprise a distance 53 between the channel 50 and the rim 40 at the minimum 26 that may be within a range of about five percent to about fifty percent of a height "H" of the cup member 10. For example, the distance 53 between the channel 50 and the rim 40 at the minimum 26 may be within a range of about ten percent to about forty percent, or about fifteen percent to about thirty percent of the height H of the cup member 10. Specifically, the distance 53 may be about twenty percent to about twenty-five percent of the height H of the cup member 10.

Conversely, a distance 55 between the channel 50 and the rim 40 at the maximum 24 may be within a range of about fifty percent to about ninety-five percent of the height H of the cup member 10. For example, the distance 55 between the channel 50 and the rim 40 at the maximum 24 may be within a range of about sixty percent to about ninety percent, or about seventy percent to about eighty-five percent of the height H of the cup member 10. Specifically, the distance 55 may be about eighty percent to about eighty-four percent of the height H of the cup member 10.

Referring back to the recessed channel 50 illustrated in FIG. 8, the first and second tapered walls 54, 56 may taper in a proximal to distal direction. The tapered walls 54, 56 may define an opening 51, sometimes referred to herein as an entrance 51, of the recessed channel 50 at an end, such that an undercut area 57 may be formed beneath the opening 51 of the recessed channel 50. It will be appreciated that the recessed channel 50 may be dimensioned such that a width of the opening 51 may be smaller than a width of the recessed surface 52. In other words, there may be at least one channel 50 formed within the outer surface 20 of the cup member 10, and the at least one channel 50 may comprise the entrance 51, the bottom 52, and a dovetail undercut 57 such that the bottom 52 of the channel 50 may be wider than the entrance 51 of the channel 50 for receiving the fixation material thereinto to thereby enhance fixation between the cup member 10, fixation material and the patient's bone.

The undercut area 57 may be configured and arranged for receiving the fixation material therein, thereby forming a mechanical lock between said fixation material and the tapered walls 54, 56 of the recessed channel 50, such that the fixation of the cup member 10 within the socket of the bone may be enhanced. Those of skill in the art will appreciate that such an undercut area 57 may or may not be present, without departing from the scope of the present disclosure.

It will be appreciated that a plurality of spacers 60 may be disposed on the outer convex surface 20 of the cup member 10. FIG. 8 illustrates an enlarged cross-sectional view of one of the plurality of spacers 60, which may be configured and arranged for creating an even mantle of fixation material between the outer convex surface 20 of the cup member 10 and the socket of the patient's bone. As illustrated, each spacer 60 may be formed integrally with the cup member 10 and may comprise an outer wall 62 that may define the shape of the spacer 60. The outer wall 62 may be essentially an extension of the outer convex surface 20 of the cup member 10. However, it will be appreciated that the spacers 60 may also be modular, without being integrally formed with the outer convex surface 20, without departing from the scope of the present disclosure. It will further be appreciated that each spacer 60 may be located distally below the channel 50, as illustrated, inter alia, in FIG. 8. However, it will be appreciated that each spacer 60 may be located proximally relative to the channel 50 without departing from the scope of the present disclosure.

FIG. 8 also illustrates the spacer 60 as having an undercut surface 64, located between a top surface 66 of the spacer 60 and the outer surface 20 of the cup member 10. It should be noted that while the spacer 60 may comprise the undercut surface 64, such an undercut surface 64 is not necessary to perform the major function of the spacer 60, i.e. to form an even mantle of fixation material. However, the presence of the undercut surface 64 may provide additional strength to the fixation between the cup member 10 and the fixation material. As the cup member 10 is located in the socket of the bone, the spacer 60 contacts the bone prepared with a layer of fixation material, and the fixation material may flow beneath the top surface 66 of the spacer 60 and enter into an undercut area defined between the top surface 66 of the spacer 60 and the outer surface 20 of the cup member 10, such that a mechanical lock between the spacer 60 and the fixation material may be formed, thereby enhancing the fixation between the fixation material and the cup member 10.

Each of the spacers 60 may rise above the level of both the first raised portion 80 and the second raised portion 82, and may be dimensioned in varying heights such that various mantle thicknesses may be achieved. In other words, each of the spacers 60 may extend above the outer surface 20 at least 2 mm. For example, it may be advantageous to create the mantle in a thickness that is at least 2 mm, which may require the spacers 60 to be at least 2 mm in height. It should be noted, however, that a mantle thickness of less than 2 mm may be achieved by decreasing the height of the spacers 60, or a mantle thickness greater than 2 mm may be achieved by increasing the height of the spacers 60. It will be appreciated that the height of the spacers 60 may correspond to the desired mantle thickness and may be modified to accommodate any desired mantle thickness.

The plurality of spacers 60 may be located distally to a relative maximum 24 of the recessed channel 50 on the outer convex surface 20, and may be formed within the second raised portion 82. However, the spacers 60 may be located and formed within the first raised portion 80, without departing from the scope of the present disclosure. It will be appreciated that the present disclosure may utilize any number of spacers 60 to create the even mantle of fixation material. However, applicants have discovered that four (4) spacers 60 evenly spaced, and located distally to the relative maximum 24 on the outer convex surface 20 of the cup member 10 may advantageously provide the desired mantle of fixation material.

Figure 9:
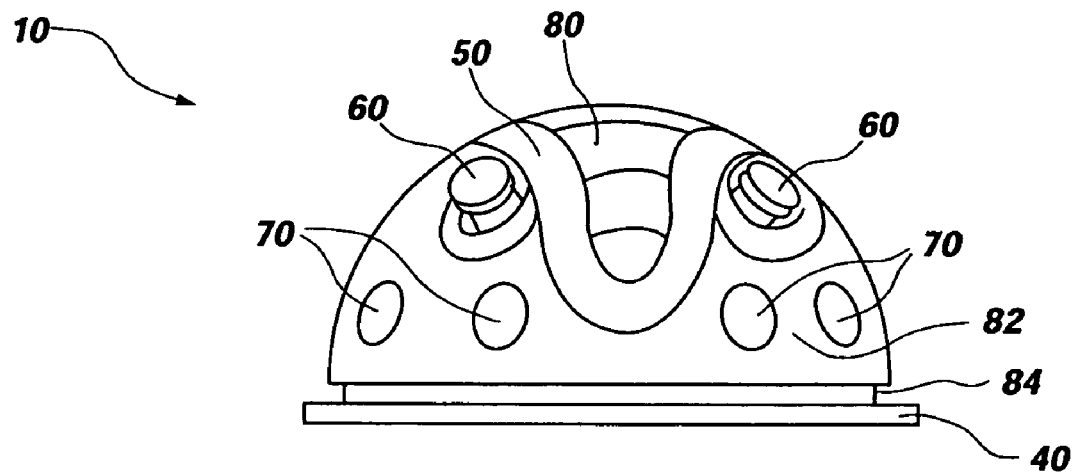
FIG. 9 is a side view of an alternative embodiment of the present disclosure, made in accordance with the principles of the present disclosure.

FIGS. 9 and 10 illustrate an alternative embodiment of the cup member 10 of the present disclosure. It will be appreciated that like reference numerals have been used to indicate like structure, where appropriate, with the previous FIGS. 1-8. As is apparent from a thorough study of the FIGS., the main difference between the present embodiment and the previous embodiment of the cup member 10 may be found in the rim 40. The rim 40 may comprise the hood 90 as in the previous embodiment, or the rim 40 may be planar without a hood 90 as illustrated in FIGS. 9 and 10. Whether the rim 40 may be formed planar without the hood 90, or whether the rim 40 may be formed with the hood 90, the rim 40 may still comprise the lead-in chamfer 42 surrounding the opening 34.

Figure 11:
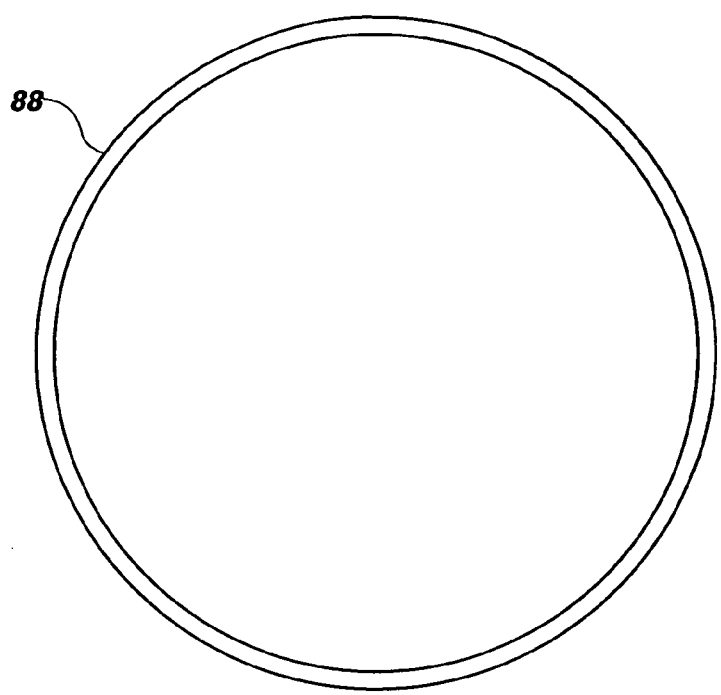
FIG. 11 is a side view of one embodiment of a marker, made in accordance with the principles of the present disclosure.
Figure 12A:
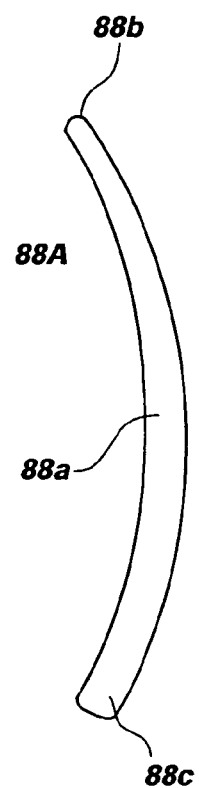
FIG. 12 is a side view of an alternative embodiment of the marker, made in accordance with the principles of the present disclosure.
Figure 12:
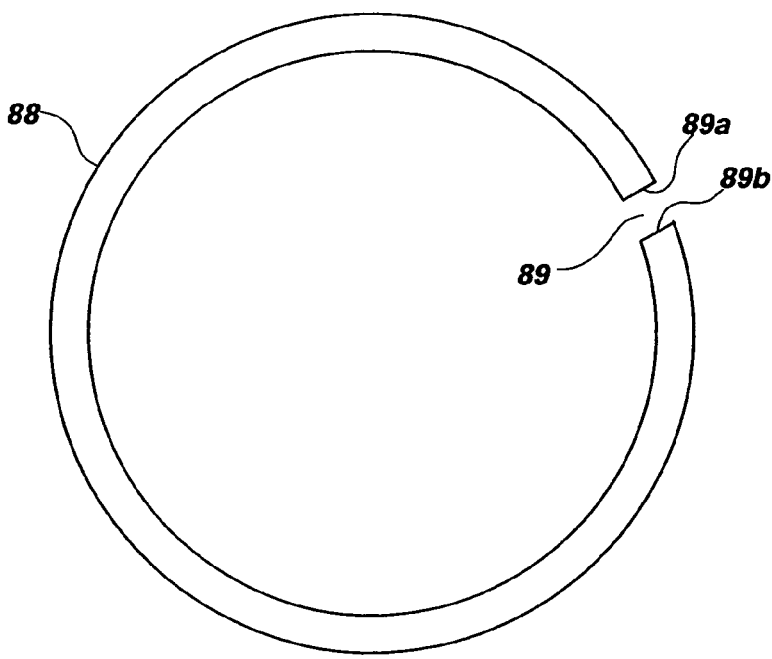

It will be appreciated that FIGS. 11 and 12 illustrate examples of the marker 88 of the present disclosure, which may be referred to herein as a first marker 88. The marker 88 illustrated in FIGS. 11 and 12 may be configured and arranged to be formed within, press-fit wholly or partially into, or received in, the first groove 84. It will be appreciated that the present disclosure may also comprise a marker 88A, which may be referred to herein as a second marker 88A or a polar marker 88A, that may be configured and arranged to be formed within, press-fit wholly or partially into, or received in the second groove 86. It will be appreciated that the marker 88 that may be configured and arranged to be located within the first groove 84 may be shaped differently than the marker 88A that may be configured and arranged to be located within the second groove 86. It will be appreciated that the difference in shape of the two markers 88 and 88A may be due to the differing shapes of each of the grooves 84 and 86 into which each of the markers 88 and 88A may be received. It will be appreciated that the markers 88 and 88A may function to assess the amount of wear in the polymeric material over time, in addition to assessing part migration over time. It will be appreciated that the principles relating to the marker 88 may be equally applied to the marker 88A, and vice-versa, without departing from the scope of the present disclosure.

FIG. 11 specifically illustrates the marker 88 as a continuous wire forming a ring and having no break. Conversely, FIG. 12 illustrates the marker 88 as a discontinuous wire having a break or gap 89 in the marker 88, allowing the marker 88 to be expanded or contracted to fit within the groove 84. The marker in FIG. 12 may also comprise a first end 89a and a second end 89b, which may be separated by and define the gap 89. It will be appreciated that the markers 88 and 88A of the present disclosure may be a wire, a ring, or any other material object that may be used to be seated within the one or more of the grooves 84 and 86. For example, the markers 88 and 88A may comprise a suitable radio-opaque material.

It will further be appreciated that the markers 88 and 88A may be manufactured from a metallic material, such that the markers 88 and 88A may be visible in an X-ray film, ultrasound, or any other medical procedure used for viewing the internal organs and tissues of the human body, utilizing appropriate medical equipment. However, it should be noted that the markers 88 and 88A may be manufactured from other materials beside metal, as long as the material possesses the characteristic properties that may permit the markers 88 and 88A to be visualized within the cup member 10 after said cup member 10 has been implanted or secured within the socket of the patient's joint. The markers 88 and 88A may thus aid the physician in positioning the cup member 10 in the socket of the bone during surgery, and subsequently locating the position of the cup member 10 during later visits or for subsequent surgeries.

It will be appreciated that the structure and apparatus disclosed herein is merely one example of a means for visualizing the cup member, and it should be appreciated that any structure, apparatus or system for visualizing the cup member which performs functions the same as, or equivalent to, those disclosed herein are intended to fall within the scope of a means for visualizing the cup member, including those structures, apparatus or systems for visualizing the cup member, which are presently known, or which may become available in the future. Anything which functions the same as, or equivalently to, a means for visualizing the cup member falls within the scope of this element.

It will be appreciated that the cup member 10 may be used during surgery in the following manner. First, the patient's joint may be dislocated. Next, the surgeon may ream a substantially spherical socket in the patient's acetabulum, exposing bleeding bone, to substantially correspond to the outer diameter of the cup member 10 using a spherical reamer (not illustrated) or other surgical instrument. Then, an amount of fixation material may be added to the bleeding bone (if the fixation material is cement, or this step may be skipped if the fixation material used is bone that may grow into the implant). Last, the cup member 10 may be inserted into the substantially spherical socket, such that the spacers 60 may contact the bleeding bone to form an even mantle of fixation material between the outer surface 20 of the cup member 10, the spacers 60 and the substantially spherical socket of the bone.

It will be appreciated that the polymeric cup member 10 may be used in the following situations: (i) in low cost, low demand patients that are typically older patients that are not as active as younger, higher demand patients; (ii) in young, high demand patients that are active; and (iii) in revision surgeries. During revision surgeries, the cup member 10 of the present disclosure may be used in a modular shell that is securely implanted within a patient's acetabulum, as there are times when only the bearing surface has worn out or failed, but the modular shell is still secured very well within the acetabulum. In this situation, the cup member 10 of the present disclosure may be located within the modular shell. In practice, the surgeon may remove the old liner, roughen the inner surface of the modular shell, and then cement the cup member 10 of the present disclosure into the modular shell to secure the cup member 10 to the modular shell.

In accordance with the features and combinations described above, a useful method of implanting a prosthetic device into a socket of a bone includes the steps of:

(a) providing a cup member comprising:

an outer convex surface and an opposing inner concave surface, said outer convex surface is configured and arranged for attaching to a fixation material, thereby securing the cup member to the socket of the patient's bone, said inner concave surface defining a substantially partially-spherical bearing cavity;

rim substantially surrounding an opening to the bearing cavity;

a channel formed in the outer convex surface defined by a recessed surface, a first wall, and a second wall, said channel having at least one minimum and at least one maximum relative to said rim, wherein a distance between the rim and the channel varies between the at least one minimum and the at least one maximum;

(b) preparing the socket of the bone to receive the cup member;

(c) forming a layer of fixation material in the prepared socket of the bone; and (d) implanting said cup member within the prepared socket of the bone such that the outer convex surface engages the fixation material securing the cup member to the socket of the bone.

Those having ordinary skill in the relevant art will appreciate the advantages provided by the features of the present disclosure. For example, it is a potential feature of the present disclosure to provide a cup member that may be directly implanted within the socket of the bone without the need for any additional components, such as a shell. It is a further potential feature of the present disclosure to provide a cup member having a curvilinear channel comprising an undercut surface that permits the fixation material to flow and enter therein providing a mechanical lock, and enhancing fixation of the cup member.

Another potential feature of the present disclosure may be to provide a curvilinear channel that may extend across the outer convex surface of the cup member having at least one minimum and at least one maximum relative to a rim, such that a distance between the rim and the channel may increase to the maximum and then decrease to the minimum in relation to said rim. It is a further potential feature of the present disclosure to provide a cup member having a plurality of divots formed in the outer convex surface of the cup member to enhance fixation of said cup member.

It is another potential feature of the present disclosure to provide a cup member having a hood extending below the rim of the cup member, and a location feature for aiding a physician in positioning and locating the hood within the socket of the bone. It is another potential feature of the present disclosure to provide at least one grooves, which may be a circumferential groove or a longitudinal groove, both of which may be configured and arranged for receiving a marker therein such that the cup member may be visualized by proper medical equipment.

It is a further potential feature of the present disclosure to provide a cup member having a plurality of spacers integrally or modularly formed with the cup member, that extend outwardly from the outer convex surface of the cup member.

It will be appreciated that in the foregoing Detailed Description, various features of the present disclosure are grouped together in a single embodiment for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed by this reference, with each claim standing on its own as a separate embodiment of the present disclosure.

It is to be understood that the above-described arrangements are only illustrative of the application of the principles of the present disclosure. Numerous modifications and alternative arrangements may be devised by those skilled in the art without departing from the spirit and scope of the present disclosure and the appended claims are intended to cover such modifications and arrangements. Thus, while the present disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. An acetabular cup member for direct implantation into a patient's bone, the cup member comprising:
   an outer convex surface and an opposing inner concave surface, wherein said outer convex surface is configured for being attached to a fixation material, thereby securing the cup member to the patient's bone, wherein said inner concave surface defines a substantially partially-spherical bearing cavity;
   a terminal edge substantially surrounding an opening to the bearing cavity, wherein the terminal edge is planar;
   a recessed surface formed in the outer convex surface defined by a first wall and a second wall and together forming a continuous channel, the channel having at least one minimum and at least one maximum relative to the terminal edge, such that the channel increases to the maximum and then decreases to the minimum in relation to said terminal edge;
   wherein the first and second walls of the channel taper outwardly from the outer convex surface in a proximal to distal direction such that the first and second walls undercut the outer convex surface permitting the fixation material to enter therein, thereby enhancing the fixation between the cup member and the fixation material through formation of a mechanical lock;
   wherein the outer convex surface comprises a first raised portion and a second raised portion relative to said channel, said channel separating the first raised portion located inside of the first and second walls of the channel from the second raised portion located outside of the first and second walls;
   wherein the channel extends around the outer convex surface in multiple planes;
   wherein the recessed surface and the first and second walls of the channel form one continuous track that extends around the outer convex surface;
   wherein the channel is curvilinear;
   wherein the channel comprises rounded, smooth edges and is characterized by the absence of sharp edges that create stress risers that potentially cause the cup member to loosen from the surrounding mantle of fixation material;
   wherein the cup member further comprises a plurality of spacers extending above the outer convex surface, wherein the plurality of spacers are configured and dimensioned for providing an even mantle of the fixation material, wherein the plurality of spacers are integrally formed on the cup member;
   wherein the cup member further comprises a plurality of divots located within the outer convex surface, wherein each of the divots comprises a recessed surface and a wall defining an opening, the wall of the divot comprising a taper that tapers in the proximal to distal direction forming an undercut area, wherein the undercut area permits the fixation material to enter therein forming a mechanical lock between said fixation material and said divot, thereby enhancing the fixation between the cup member and the fixation material;
   wherein the cup member is made entirely of a polymeric material;
   wherein the outer convex surface of the cup member comprises a pole;
   wherein the cup member comprises a first groove formed circumferentially around the terminal edge;
   wherein the cup member comprises a first marker that circumferentially extends around the terminal edge and is located within the first groove adjacent and proximally to the terminal edge;

wherein the cup member comprises a second, longitudinal groove formed in the outer convex surface that extends from one side of said cup member through the pole to another side of the cup member;

wherein the cup member comprises a polar wire that is positionable within the second, longitudinal groove;

wherein the cup member comprises four part symmetry; and wherein the cup member further comprises a lead-in chamfer formed at a junction between the inner concave surface and the terminal edge of said cup member, wherein the lead-in chamfer provides an enhanced range of motion for a prosthetic femoral head.

* * * * *

UNITED STATES PATENT AND TRADEMARK OFFICE
CERTIFICATE OF CORRECTION

PATENT NO.         : 7,402,177 B2
APPLICATION NO. : 11/192513
DATED                   : July 22, 2008
INVENTOR(S)        : Scott A. Jones et al.

It is certified that error appears in the above-identified patent and that said Letters Patent is hereby corrected as shown below:

Column 2, Line 63 reads, "There is a long felt, but unmet need, for..." which should read, "There is a long-felt, but unmet, need..."

Column 2, Line 63 reads, "...simple in operation and that enhances..." which should read, "...that is simple in operation and that enhances..."

Column 3, Line 30 reads, "FIG 5 is side view..." which should read, "FIG 5 is a side view..."

Column 8, Line 34 reads, "...member 10 may comprise a plurality of divots..." which should read, "...member 10 may comprise a plurality of divots..."

Column 8, Line 67 reads, "...defined by surface 72 may be formed..." which should read, "...defined by surface 74 may be formed..."

Column 11, Line 64 reads, "...it will be appreciated each of the channels..." which should read, "...it will be appreciated that each of the channels..."

Column 16, Line 55 reads, "rim sustainability surrounding an opening..." which should read, "a rim sustainability surrounding an opening..."

Column 17, Line 32 reads, "...to provide at least one grooves..." which should read, "...to provide at least one groove..."

UNITED STATES PATENT AND TRADEMARK OFFICE
CERTIFICATE OF CORRECTION

PATENT NO. : 7,402,177 B2
APPLICATION NO. : 11/192513
DATED : July 22, 2008
INVENTOR(S) : Scott A. Jones et al.

It is certified that error appears in the above-identified patent and that said Letters Patent is hereby corrected as shown below:

Column 17, Line 51 reads, "...incorporated into this Detailed by this reference..." which should read, "...incorporated into this Detailed Description by this reference..."

Signed and Sealed this

Twenty-fourth Day of November, 2009

David J. Kappos
*Director of the United States Patent and Trademark Office*